United States Patent [19]

Yamamoto et al.

[11] Patent Number: 5,448,610
[45] Date of Patent: Sep. 5, 1995

[54] DIGITAL X-RAY PHOTOGRAPHY DEVICE

[75] Inventors: Kazuo Yamamoto, Ibaraki; Masami Shimizu, Ichikawa; Joichi Tamura; Shyunpei Nishimura, both of Ibaraki, all of Japan

[73] Assignee: Hitachi Medical Corporation, Tokyo, Japan

[21] Appl. No.: 191,530

[22] Filed: Feb. 4, 1994

[30] Foreign Application Priority Data

Feb. 9, 1993 [JP] Japan .................................. 5-043369
Mar. 19, 1993 [JP] Japan .................................. 5-083903

[51] Int. Cl.⁶ ............................................. H05G 1/60
[52] U.S. Cl. ............................................ 378/19; 378/4
[58] Field of Search ..................................... 378/19, 4

[56] References Cited

U.S. PATENT DOCUMENTS 4,991,190  2/1991  Mori .................................... 378/19

FOREIGN PATENT DOCUMENTS 2-156778  2/1990  Japan .
3-55040   3/1991  Japan .

Primary Examiner—Craig E. Church
Attorney, Agent, or Firm—Antonelli, Terry, Stout & Kraus

[57] ABSTRACT

A digital X-ray photography device, including an X-ray tube unit, a rotation supporting unit for rotating around a subject, an image system unit installed on the rotation supporting unit, for detecting X-rays transmitted through the subject, a first image processing unit, installed on the rotation supporting unit, for constructing a rotational stereoscopic image of the subject based on a signal from the image system unit, an X-ray detector, installed on the rotation supporting unit, for detecting X-rays transmitted through the subject, a second image processing unit, installed on the rotation supporting unit, for constructing a CT image of the subject based on a signal from the X-ray detector, and a unit for controlling pulse-shaped X-rays to be continuously radiated during a forward rotation and a backward rotation of the rotation supporting unit in order to perform a rotational stereoscopic photographing.

8 Claims, 5 Drawing Sheets

DIGITAL X-RAY PHOTOGRAPHY DEVICE

BACKGROUND OF THE INVENTION

The present invention relates to a digital X-ray photography device for taking an X-ray photograph by detecting X-rays which have been transmitted through a subject by radiating X-rays on to the subject while rotating an X-ray tube unit and an image detecting system around the subject on a table, and obtaining inspection images of a portion to be diagnosed of the subject, and relates more particularly to a digital X-ray photography device which can easily execute an inspection of the diagnosed portion of the subject by discriminating between a rotational stereoscopic photography and a tomography by one set of X-ray photography device.

According to the digital X-ray photography device of the present invention, it is possible to reduce time required for taking an X-ray photograph by rotating the X-ray tube unit and an image system unit for taking an X-ray photograph around a subject, and it is also possible to always observe the status of the subject.

According to a conventional digital X-ray photography device, within a gantry, installed on a floor surface, having an opening for inserting thereinto a table of a subject in a horizontal direction at about the center of a standing portion, the X-ray tube unit and the image detecting system are disposed face to face, in a one to one relationship, on a ring-shaped rotation supporting unit provided rotatably around the opening, with the rotation center of the rotation supporting unit sandwiched between the X-ray tube unit and the image detecting system. Further, two units have been structured independently as separate unites; an X-ray CT unit for obtaining two-dimensional tomograms which are sliced images of the diagnosed portion of the subject, photographed by rotating the rotation supporting unit around the subject, and an X-ray rotational stereoscopic photographing unit for observing the diagnosed portion as stereoscopic images by displaying the photographed images around the diagnosed portion as a dynamic picture.

Since the X-ray CT unit and the X-ray rotational stereoscopic photographing unit have been independently structured as separate units in the conventional digital X-ray photography device as described above, in the case of installing these two units in the same facility (such as a hospital), it has been necessary to have two independent photographing rooms equipped with X-ray shielding walls or it has been necessary to have a widespaced photographing room sufficiently wide enough to accommodate the two units with a common X-ray shielding wall provided in the room. Therefore, any one of the above alternative cases has required a wide space and costs for accommodating the two units, resulting in a costly arrangement.

Further, in the case of executing both the inspection by the X-ray rotational stereoscopic photographing unit and the inspection by the X-ray CT unit for a subject to be tested who requires an urgent diagnosis and treatment at a first aid and lifesaving facility or the like, for example, it has been necessary to carry the subject on a stretcher to a photographing room where one of the units is installed, move the subject to a table for the subject for this unit to carry out an inspection by an X-ray irradiation, then to place the subject on the stretcher to carry the subject to a photographing room where the other unit is installed, and move the subject to a table for the subject for this unit to carry out an X-ray irradiation. In this case, moving the subject between the photographing rooms and moving the subject from one table to the other forces a heavy load on the subject if the subject is in a seriously ill state, and accordingly it has been dangerous to move the subject. Further, in addition to the time required for actual inspections, it also takes time to carry the subject and move the subject between the tables of the respective units, and in order to carry out this operation in safe and in short time, many skilled operators and assistants have been required.

As examples of the conventional digital X-ray photography device, there are, for example, the Japanese Patent Unexamined Publication No. 2-156778 (a first prior art example) and the Japanese Patent Unexamined Publication No. 3-55040 (a second prior art example).

According to the above-described first and second conventional embodiments, in the case of carrying out a blood vessel fluoroscopic inspection, a rotation supporting unit is rotated around the subject and X-rays are simply radiated to the subject at the time of a forward rotation of the X-ray tube unit and the image system unit to take a photograph of the transmitted X-rays, then the X-ray tube unit and the image system unit are returned to an initial reference position by a backward rotation. Next, a contrast medium is injected into the subject by using a catheter and then the rotation supporting unit is started to take a photograph of the X-rays transmitted through the subject by the X-ray tube unit and the image system unit during a forward rotation this time after the contrast medium has been injected. Accordingly, it has been necessary to have a time for returning the X-ray tube unit and the image system unit to the initial reference position by a reverse rotation of these units. Thus, it has taken a long time to finish the whole photographing operation and therefore it has taken a long time for binding the subject, with a result of an increase in psychological burden on the subject in some cases. Further, during the period while the X-ray tube unit and the image system unit are being returned by a backward rotation, the transmitted X-ray image of the subject can not be obtained and operators such as radiologists can not observe the status of the subject, so that there has been an anxiety that this system can not meet a sudden change in the status of the subject.

Further, according to the first conventional example, two sets of television monitors are used as display units and two images having a predetermined phase difference, or a difference of rotation angle of the rotation supporting unit, obtained by an image picked up during the forward rotation are simultaneously displayed on the television monitors. Since an operator such as a radiologist watches this display with both eyes to have a stereoscopic view, it has not been possible for many people to simultaneously observe a stereoscopic image.

Further, according to the second conventional example, a so-called C arm or a U arm has been used as a rotation supporting unit, and the arm is exposed and the reproducibility of the position of the arm during a rotation has not been satisfactory, with a result that the rotation speed during a photographing period has been restricted to as low as 10 degrees per second, for example. Accordingly, time required for the whole photographing operation has been longer and an injection of the contrast medium into the subject has had to be for long time, with a result that pains are applied to the subject in some cases. Therefore, in order to reduce the photographing time, it has been necessary to take some actions such as to limit the range of an angle for taking an X-ray photograph of the subject, with a result that sufficient diagnosis information can not be obtained in some cases.

SUMMARY OF THE INVENTION

In order to overcome the above-described problems, it is an object of the present invention to provide a digital X-ray photography device which can easily carry out an inspection of a portion of a subject with one set of device by discriminating the use of a rotational stereoscopic photography and a tomography.

Further, it is another object of the present invention to provide a digital X-ray photography device which can reduce time required for taking an X-ray photograph by rotating an X-ray tube unit and an image system unit around a subject and which makes it possible to always observe the status of the subject.

In order to achieve the above-described objects, the digital X-ray photography device according to the present invention includes a body gantry installed on a floor surface and having an opening for inserting thereinto a table for a subject in a horizontal direction at about the center of a standing portion, a ring-shaped rotation supporting unit provided rotatably around the opening within the body gantry, an X-ray tube unit for radiating X-rays to the subject, provided movably on this rotation supporting unit by a range of a predetermined angle around the rotation center of the rotation supporting unit, an image system unit fixed at a predetermined position on the rotation supporting unit for converting a transmitted X-ray image of the subject into an optical image and taking an X-ray photograph of the output of this optical image and converting this image into an image signal, an X-ray detector fixed at other predetermined position on the rotation supporting unit for detecting transmitted X-rays of the subject and converting these X-rays into an electric signal, a first image processing unit for digitalizing the image signal from the image system unit and processing this digital signal to construct an image, a second image processing unit for digitalizing an electric signal from the X-ray detector and processing this digital signal to reconstruct a tomogram, one or a plurality of display units for inputting image signals from these image processing units respectively and displaying images, a body control unit for controlling a rotation operation of the rotation supporting unit and a move operation of the X-ray tube unit, and a system control unit for controlling the operation of each of the above-described structural elements.

In the digital X-ray photography device structured as described above, the X-ray tube unit is moved on the rotation supporting unit so as to face from the front the image system unit or the X-ray detector which are fixed at different predetermined positions on the rotation supporting unit, and X-rays are radiated to the subject on the table from the X-ray tube unit by rotating the rotation supporting unit, to pick up a rotational stereoscopic image or a tomogram of the portion to be diagnosed.

Further, the body control unit controls the rotation supporting unit to be able to make a forward rotation or a backward rotation at a desired angle when an image of a blood vessel is to be taken by injecting a contrast medium into the blood vessel, for example, and the system control unit controls so that pulse-shaped X-rays are continuously radiated from the X-ray tube unit throughout the period of a forward rotation, a backward rotation and a reversed rotation from a forward rotation to a backward rotation, including a period of a deceleration, a stopping and an acceleration so that a time taken for a rotational stereoscopic photography can be reduced and the status of the subject can always be observed.

In this case, the first image processing unit is structured to generate display image data by calculating using image data at the same mechanical phase angle or rotational phase angle that have been taken at times of a forward rotation and a backward rotation of the rotation supporting unit.

Further, the system control unit is structured to repeat a forward rotation and a backward rotation of the rotation supporting unit by a desired number of times and pulse-shaped X-rays are radiated continuously during this repeated period.

With the above-described structure of the present invention, it is possible to carry out an inspection easily by discriminating the use of a rotational stereoscopic photography and a tomography of the portion to be diagnosed of the subject in one set of the device. Accordingly, space for two sets of device is not required as has been the case with the conventional system, and the device can be installed efficiently spacewise for one set of device. It is not necessary to move the subject between the tables of the respective units and it is possible to carry out diagnosis and treatment of the subject safely and quickly.

Further, when an image of a blood vessel is taken before and after a contrast medium is injected into the subject by rotating the X-ray tube unit and the image system unit, it is not necessary to return the X-ray tube unit and the image system unit to an initial reference position by reversing these units each time, so that time required for finishing the whole photographing process can be reduced. Thus, it is possible to reduce time of binding the subject and to reduce psychological burden of the subject. Further, since it is possible to obtain images of X-rays transmitted through the subject during a period while the X-ray tube unit and the image system unit are being made a backward rotation and during a period of a reversed rotation from a forward rotation to a backward rotation, an operator such as a radiologist can always observe the whole status of the subject during the inspection period so that the operator can take a quick action against a sudden change in the status of the subject. Because of the above-described characteristics, it is possible to improve a clinical value of the digital X-ray photography device.

DESCRIPTION OF THE PREFERRED EMBODIMENTS

Embodiments of the present invention will be explained in detail with reference to the attached drawings.

Figure 1:
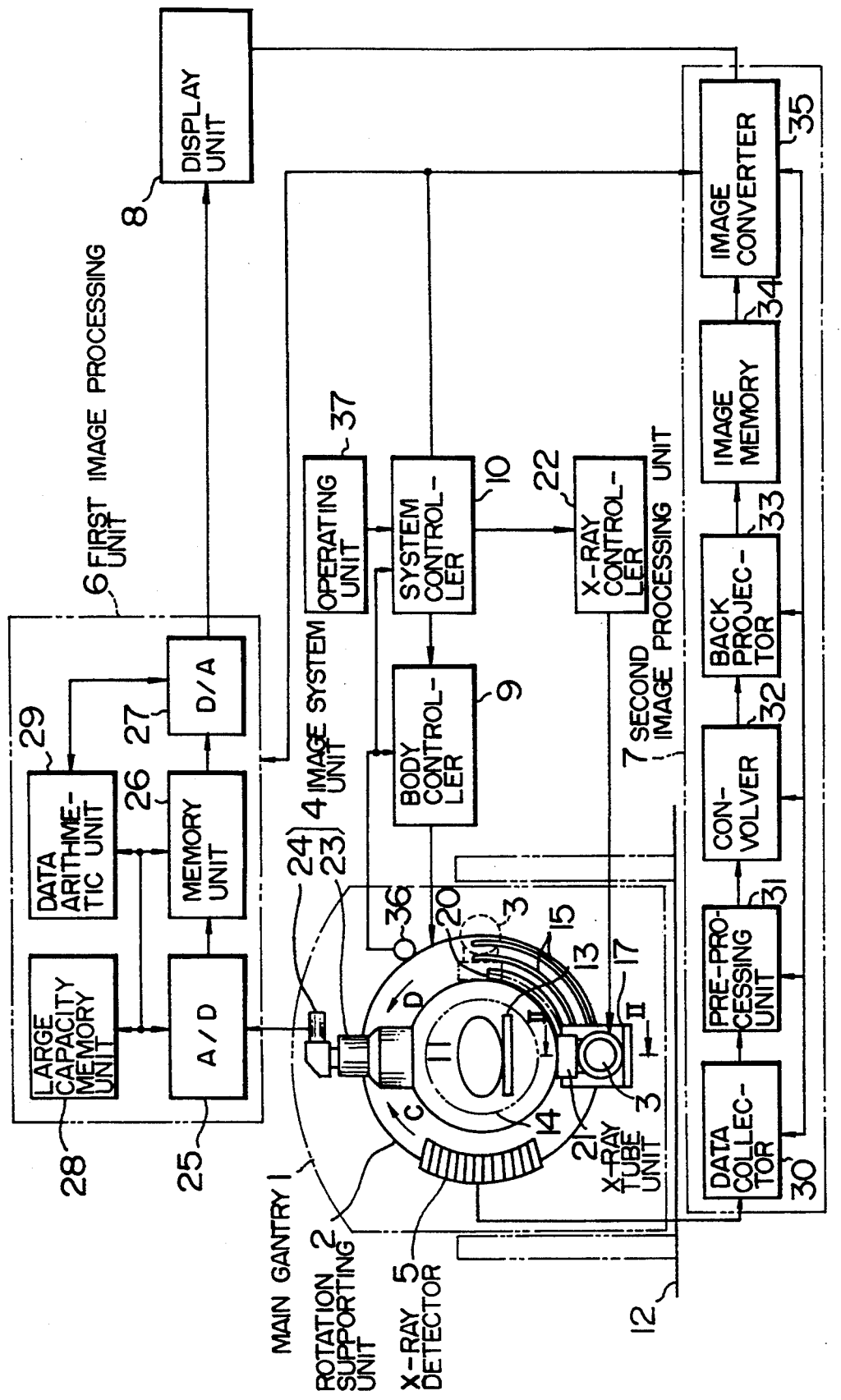
FIG. 1 is a block diagram for showing an embodiment of the digital X-ray photography device according to the present invention.

FIG. 1 is a block diagram for showing an embodiment of the digital X-ray photography device according to the present invention. This digital X-ray photography device radiates X-rays to a subject on a table by rotating a X-ray tube unit and an image detecting system around the subject, detects transmitted X-rays and takes an X-ray photograph to obtain an inspection image by a rotational stereoscopic photography and a tomography of a portion to be diagnosed of the subject. The digital X-ray photography device includes a body gantry 1, a rotation supporting unit 2, an X-ray tube unit 3, an image system unit 4, an X-ray detector 5, a first image processing unit 6, a second image processing unit 7, a display unit 8, a body controller 9 and a system controller 10.

The body gantry 1 rotatably supports the X-ray tube unit 3, the image system unit 4 and the X-ray detecting unit 5 to be explained later, and forms a main unit for carrying out an X-ray inspection of a subject 11. The body gantry 1 is installed on a floor surface 12 and has an opening of about a circular shape formed at about the center of a standing portion for inserting a table 13 of the subject into the opening in a horizontal direction. The rotation supporting unit 2 is provided inside the body gantry 1. The rotation supporting unit 2 rotatably supports the X-ray tube unit 3, the image system unit 4 and the X-ray detector 5, and is formed in a ring shape having a rotation center at the center of the opening 14 so as to be rotatable around the opening. The rotation supporting unit 2 is provided to make forward and backward rotations in an arrow direction C or D by a known driving mechanism not shown. Assuming an angle of an irradiation of X-rays on to the subject 11 is 360 degrees as a maximum, for example, a range of a rotational angle of the rotation supporting unit 2 is set to be about 500 degrees as a maximum, for example, by adding an acceleration range for starting from a stopped position to a beginning of the X-rays radiation and a deceleration range for stopping from an end of the X-rays radiation to a stopped state to this X-rays irradiation angle.

Figure 2:
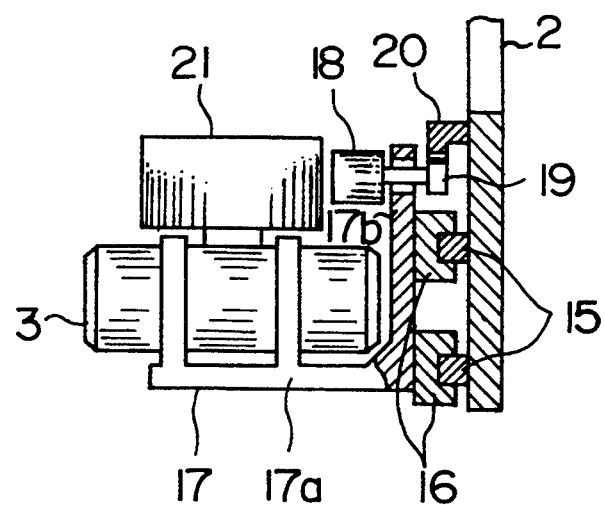
FIG. 2 is a partial cross section cut along the line II—II of FIG. 1 for showing a fitting structure of the X-ray tube unit.

The X-ray tube unit 3 radiates X-rays to the subject 11 which is loaded on the table 13, and is set on the rotation supporting unit 2 to be movable by a range of a predetermined angle around the rotation center of the rotation supporting unit 2. The X-ray tube unit 3 is moved by a mechanism structured by arc guide rails 15 and 15, moving blocks 16 and 16 and a moving table 17, as shown in FIGS. 1 and 2. The guide rails 15 and 15 are formed in parallel in arc projection at one side of the rotation supporting unit 2 around the rotation center of the rotation supporting unit 2 with a predetermined distance between the two guide rails, having an arc length of about ¼ of a circle, for example. The moving table 17 also works as a table for fixing the X-ray tube unit 3 in a movable state, and is formed in about an L shape in its side view, fixing the X-ray tube unit 3 with a extension member 17a. At the rear side of a right angle member 17b, the moving blocks 16 and 16 are provided with a distance therebetween equal to the distance of the guide rails 15 and 15. Recesses of the moving blocks 16 and 16 are engaged with the guide rails 15 and 15 respectively to move the moving table 17 along with the guide rails 15 and 15.

To drive the moving table 17, a driving motor 18 is fitted to the right angle member 17b and a pinion 19 is fixed to a rotation axis which projects piercing through the right angle member 17b, as shown in FIG. 2. The pinion 19 is engaged with an arc sector gear 20 provided parallel to the guide rails 15 as shown in FIG. 1. Accordingly, when the driving motor 18 is driven to rotate, the pinion 19 and the sector gear 20 work to move the X-ray tube unit 3, guided by the guide rails 15 and 15, within a range of about 90 degrees, for example, by keeping an X-ray radiation opening of the X-ray tube unit faced to the rotation center of the rotation supporting unit 2. At the X-ray radiation opening of the X-ray tube unit 3, a collimator 21 for collimating an X-ray beam is provided. Supply of high voltage to the X-ray tube unit 3 and the control of X-ray radiation are carried out by the X-ray controller 22.

The image system 4 converts a transmitted X-ray image of the subject 11 into an optical image and picks up an output image of this optical system for converting into an image signal. The image system 4 includes an image intensifier (hereinafter to be abbreviated as (I.I.)) 23 into which an X-ray image which has been radiated from the X-ray tube unit 3 and transmitted through the subject 11 is applied and this image is converted into an optical image, and a television camera 24 for picking up the optical image outputted from the I.I. 23 and converting the picked-up image into an electric signal. The photographing unit 4 is fixed at a predetermined position on the rotation supporting unit 2, for example, at a position which faces, across the opening 14, one of the limit positions of a movable angle range in which the X-ray tube unit 3 can move with the guide rails 15 and 15.

The X-ray detector 5 detects X-rays transmitted through the subject 11 and converts the detected X-rays into an electric signal. In order to apply X-rays having a certain wide range that have been transmitted through the subject 11 after being radiated in a fan shape, for example, from the X-ray tube unit 3 and for taking an X-ray photograph in this wide range, many detecting elements are laid out in an arc shape to form a multi-channel type. The X-ray detector 5 is fixed at another predetermined position on the rotation supporting unit 2, for example, at a position which faces, across the opening 14, the other limit position of a movable angle range in which the X-ray tube unit 3 can move with the guide rails 15 and 15. Accordingly, in FIG. 1, the image system unit 4 and the X-ray detector 5 are fixed at separate positions to form a right angle around the opening 14 on the rotation supporting unit 2. This angle is not limited to a right angle if the image system unit 4 and the X-ray detector 5 are not superimposed with each other.

The first image processing unit 6 digitalizes an image signal from the television camera 24 of the image system unit 4 and processes this digital signal to construct an image. The first image processing unit 6 includes an A/D converter 25 for inputting an analog image signal outputted from the television camera 24 and converting this signal into a digital signal, a memory unit 26 for storing image data outputted from the A/D converter 25, a D/A converter 27 for inputting image data which has been read from the memory unit 26 and converting this image data into an analog image signal again, a large-capacity memory 28 for storing a large number of image data outputted from the A/D converter 25, and a data processing unit 29 for carrying out a required operation by reading image data from the memory unit 26 and the large-capacity memory unit 28. With the above-described system, an image is constructed by carrying out a rotational stereoscopic photographing.

The second image processing unit 7 digitalizes an electric signal from the X-ray detector 5 and processes this digital signal to reconstruct a tomogram. The second image processing unit 7 includes a data collector 30 for integrating data from each channel of the X-ray detector 5 and A/D converting and storing the data, a preprocessor 31 for receiving X-ray absorbed data from the data collector 30 and carrying out preprocessing of this data, such as analog conversion, gain correction, offset correction, etc., a convolver 32 for receiving data from the preprocessor 31 and carrying out convolution operation of X-ray absorbed data in whole projection directions, a back projector 33 for inversely projecting data that have been convolved by the convolver 32 to an image memory 34 to be described later and reconstructing a superimposed tomogram, an image memory 34 for storing a tomogram that has been reconstructed by the back projector 33, and an image converter 35 for setting a CT value of a desired range for the data relating to the tomogram that has been reconstructed on the image memory 34.

The display unit 8 inputs image signals from the first image processing unit 6 and the second image processing unit 7 respectively and displays an image by a rotational stereoscopic photography or a tomography, and the display unit 8 includes one or a plurality of television monitors. The body control unit 9 controls a rotation operation of the rotation supporting unit 2 and a move operation of the X-ray tube unit 3, by inputting an actual position signal from an encoder 36 for detecting a rotation position of the rotation supporting unit 2. The system control unit 10 controls an operation of each of the structural elements, and includes a CPU (central processing unit), for example. Various types of operation commands are inputted to the system control Unit 10 from an operating unit 37.

Operation of the digital X-ray photography device having the above-described structure will be explained with reference to FIGS. 3 to 6. Description will first be made of a case of carrying out an inspection of the subject 11 by rotational stereoscopic photography and then carrying out an inspection by tomography. The subject 11 carried on a stretcher to a photographing room is moved on to the table 13 for the body, and the table 13 of the body is moved up and down and left and right to be positioned so that a desired diagnosis portion is positioned in the X-ray irradiation area. Next, the operator operates a selection switch of a rotational stereoscopic photographing mode not shown on the operating unit 37, so that the X-ray tube unit 3 moves with the guide of the guide rails 15 and 15 based on the rotation of the driving motor 18 shown in FIG. 2 and is automatically set to a position which faces the I.I. 23 of the image system unit 4 as shown in FIG. 1.

Figure 3:
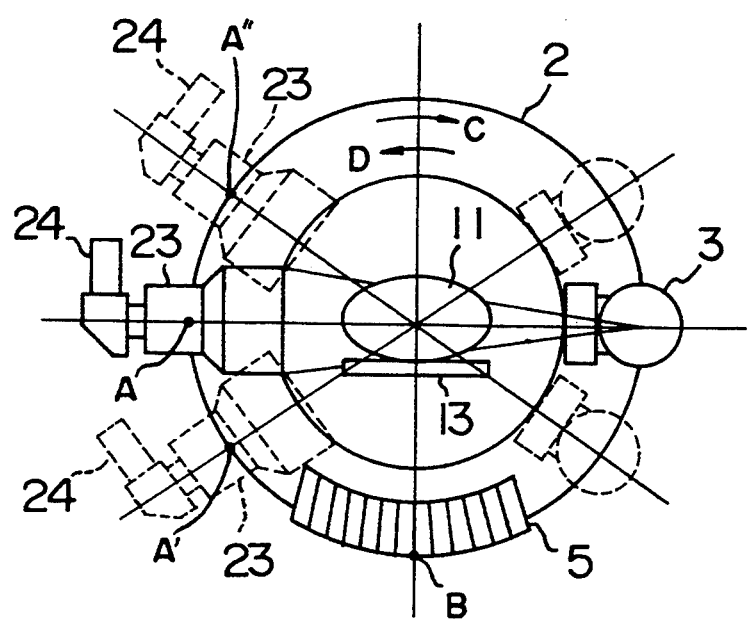
FIG. 3 is a diagram for explaining one embodiment of the rotational stereoscopic photography according to the digital X-ray photography device of the present invention.

In this state, an X-ray fluoroscopy is carried out and a catheter is introduced into a portion to be diagnosed, and then the operator operates a photographing preparatory switch not shown on the operating unit 37, so that the system controller 10 suitably rotates the rotation supporting unit 2 through the body controller 9 to move the I.I. 23 to a A' position and stops as shown in FIG. 3. In this case, the X-ray tube unit 3 is positioned at the A' point. This is the status of the waiting position before starting a photographing.

When the operator has started a photographing by the operating unit 37, the rotation supporting unit 2 starts rotation in an arrow C direction, for example, in FIG. 3 and the I.I. 23 starts operation from the A' point and the I.I. operation is accelerated and is stabilized at a predetermined rotation speed immediately before reaching the A point. In this case, the encoder 36 shown in FIG. 1 detects that the I.I. 23 has reached the A point and transmits this detection signal to the body controller 9. Then, the body controller 9 sends the detection signal to the system controller 10, and the system controller 10 sends a control signal of the starting of a photographing to the X-ray controller 22. From this point, the X-ray controller 22 generates a pulse-shaped high voltage and supplies it to the X-ray tube unit 3. With the above arrangement, pulse shaped X-rays are radiated from the X-ray tube unit 3 and irradiated to the subject on the table 13.

An X-ray image transmitted through the subject 11 is incident to the I.I. 23 and is converted into an optical image, and an output optical image is picked up by the television camera 24. An image signal from the television camera 24 is inputted to the first image processing unit 6 and is processed there as necessary. Images of the subject 11 which have been sequentially taken during the rotation in the arrow C direction shown in FIG. 3 are continuously displayed in the display unit 8. The continuous display images have different directions of X-rays irradiation to the subject for each image, and therefore these images are observed as stereoscopic images due to an after-image effect of operator's eyes.

X-ray images are picked up continuously by the X-ray tube unit 3 and the I.I. 23 as described above. When the I.I. 23 has rotated by 360 degrees in the arrow C direction in FIG. 3 to reach the A point again, the encoder 36 detects this state and the X-ray radiation from the X-ray tube unit 3 is stopped through the body controller 9, the system controller 10 and the X-ray controller 22. Then, the system controller 10 operates to stop the rotation of the rotation supporting unit 2 through the body controller 9, starting a deceleration from the A point to stop the rotation at an A" point in FIG. 3. Then, the procedure same as the above is repeated when it is necessary to take a photograph of the same portion again or an image of another portion.

Next, description will be made of a control method for reducing a photographing time when an image of a blood vessel is picked up by injecting a contrast medium into the body 11 and for making it possible to always observe the status inside the subject during an inspection.

Figure 4:
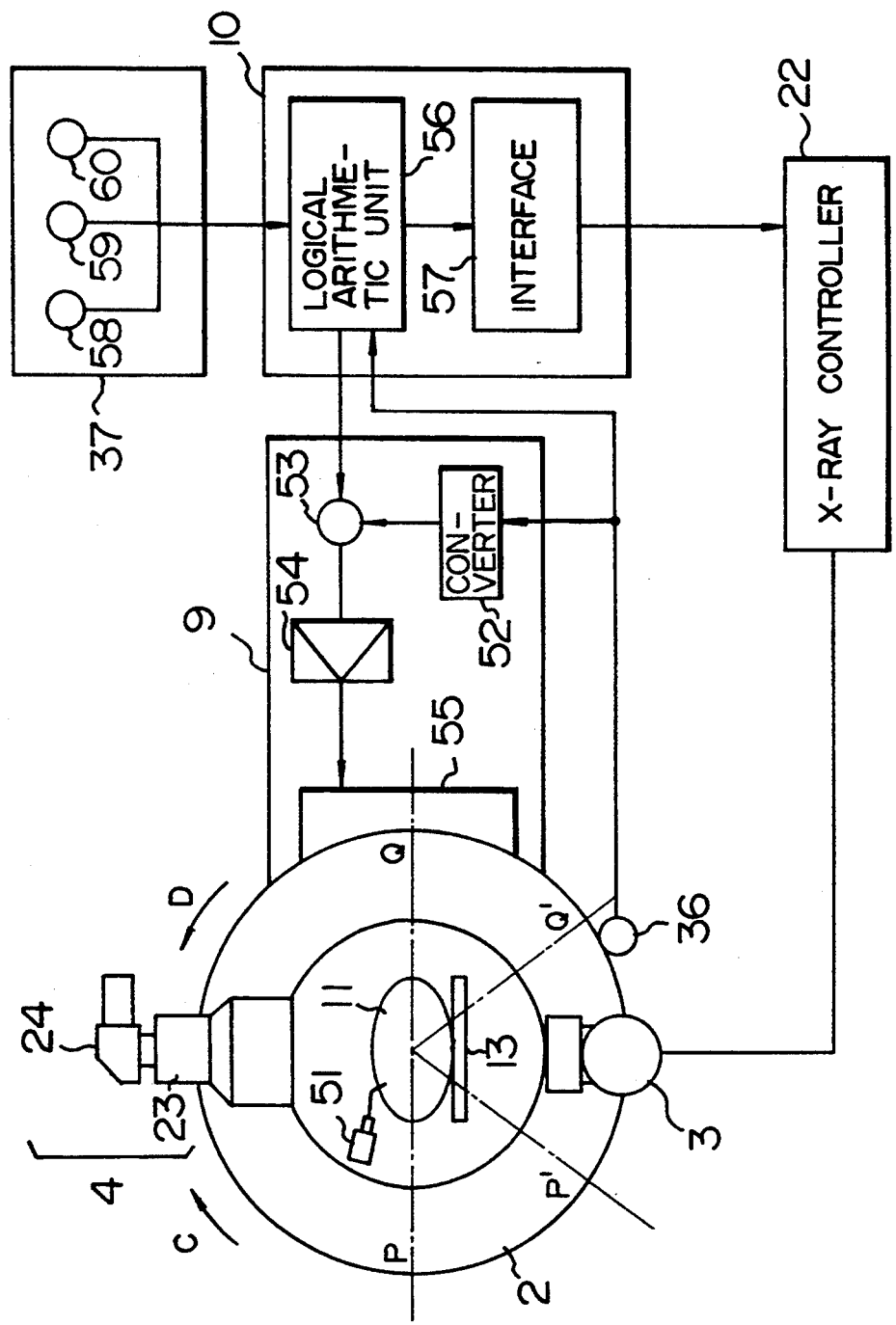
FIG. 4 is a diagram for explaining another embodiment of the rotational stereoscopic photography according to the digital X-ray photography device of the present invention.
Figure 5:
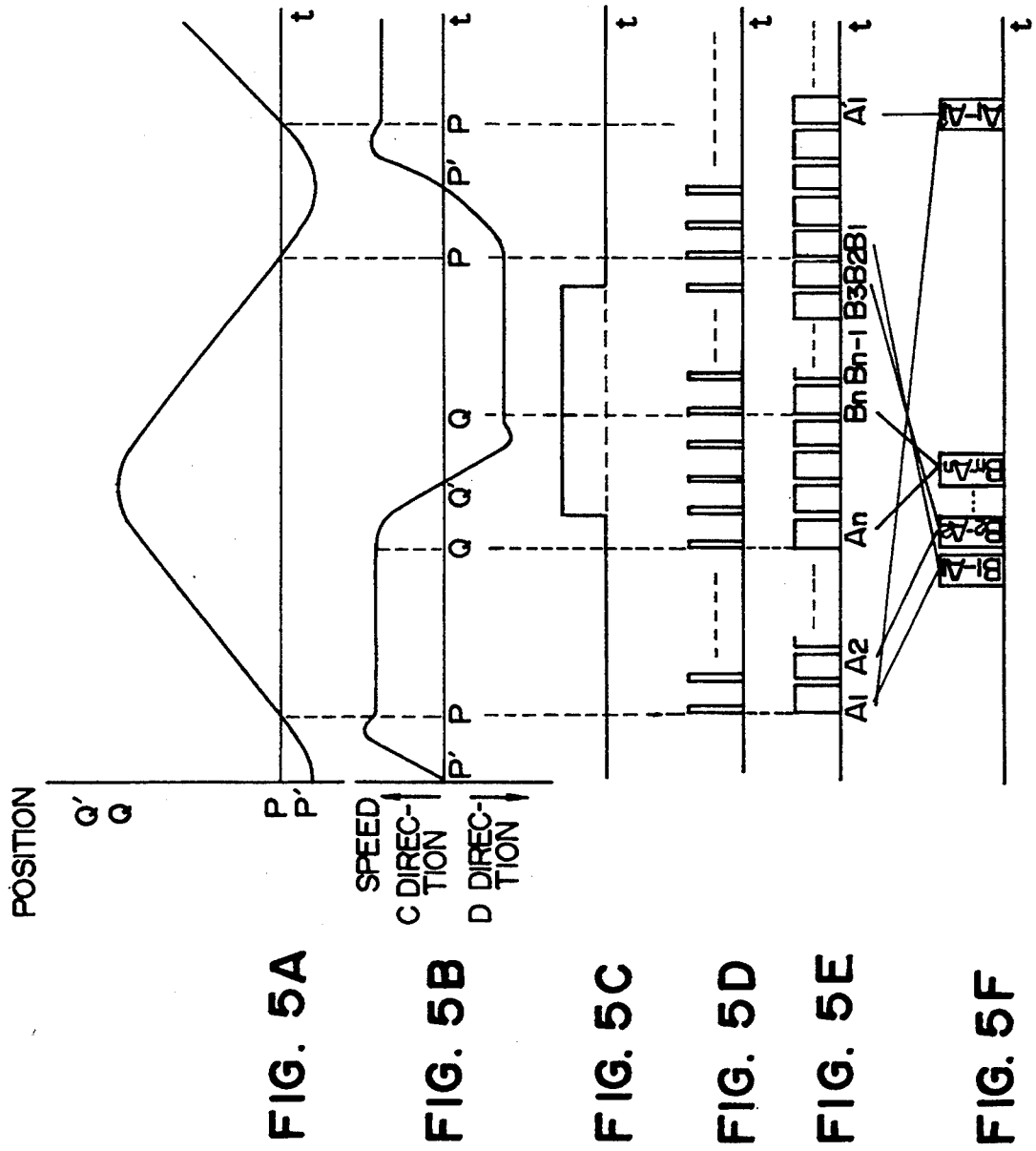
FIGS. 5A to 5F are diagrams for explaining the operation of FIG. 4.

FIG. 4 is a diagram for explaining one embodiment of the control method.

A symbol 51 designates a contrast medium injector for injecting a contrast medium into the subject 11.

As one example, the body controller 9 controls rotation supporting unit 2 to be able to make a forward rotation and a backward rotation in a desired range of angle, for example, in a range between 0 degree and 180 degrees. The body controller 9 includes a converter 52 for inputting an actual position signal of the rotation supporting unit 2 from the rotary encoder 36 and converting this signal, a comparator 53 for comparing an actual position signal of the rotation supporting unit 2 inputted from this converter 52 with a target position signal inputted from the system controller 10, a servo amplifier 54 for inputting an error signal outputted from the comparator 53 and amplifying this signal, and a driving circuit 55 including a servo motor which is operated by a driving signal from the servo amplifier 54 and drives the rotation supporting unit 2 to rotate. The system controller 10 controls so that pulse state X-rays are continuously radiated from the X-ray tube unit 3 to make it possible to continuously pick up images throughout the period of a forward rotation, a backward rotation and a reversed rotation from a forward rotation to a backward rotation of the rotation supporting unit 2. As one embodiment, the system controller 10 includes a logical arithmetic unit 5 for inputting an actual position signal of the rotation supporting unit 2 from the rotary encoder 36 and an operation command from the operating unit 37 to carry out an operation, and an X-ray control interface 57 for sending a command from the logical arithmetic unit 56 to the X-ray control unit 22. The operating unit 37 includes a photographing mode selecting switch 58, a photographing starting switch 59 and a photographing stopping switch 60 in addition to various operation switches.

Operation of the above-described case will be explained with reference to FIGS. 5A to 5F. In the following example of the operation, it is assumed that images of the subject 11 are picked up by moving the image system unit 4 over the range of 180 degrees between a P point and a Q point, where the P point is at a position of 0 degree and the Q point is at a position of 180 degrees on the rotation supporting unit 2 in FIG. 4 respectively. In FIG. 4, a P' point is a waiting position before starting the operation and a Q' point is a position for changing the rotation from a forward rotation to a backward rotation.

First, in FIG. 4, when the operator has operated the preparation switch, not shown, of the operating unit 37, to prepare for the operation, the logical arithmetic unit 56 of the system control unit 10 sends the position signal at the waiting P' point on the rotation supporting unit 2 to the comparator 53 within the body control unit 4. An actual position signal of the rotation supporting unit 2 detected by the rotary encoder 36 is inputted to this comparator 53 through the converter 52, and the comparator 53 compares these two input signals and sends an error signal between the two signals to the servo amplifier 54. Then, the servo amplifier 54 amplifies the error signal and sends this signal to the driving circuit 55 as a driving signal. Thus, the servo motor within the driving circuit 55 is driven to rotate the rotation supporting unit 2 and to move the image system unit 4 to the waiting position P' point.

Next, the operator operates the photographing mode selecting switch 58 of the operating unit 37 to set to a continuous going and returning photographing mode, for example. Then, the logical arithmetic unit 56 sequentially updates the position information in the C direction (a forward rotation direction) from the P' point to the Q' point in a predetermined acceleration pattern (ref. FIG. 5A), and produces an output to the comparator 53. Based on this operation, through an operation similar to the operation when the rotation supporting unit 2 moved to the waiting position P' point, the rotation supporting unit 2 starts a rotation in the C direction in FIG. 4 and a rotation speed curve rises from the P' point in FIG. 5B. Immediately before reaching the P point in FIG. 4, the rotation speed is accelerated to a predetermined speed, for example, 180 degrees/2 seconds. In this case, the rotation speed is settled to a predetermined speed immediately before reaching the P point, as shown in FIG. 5B. Thereafter, position information is updated in a predetermined cycle as shown in a straight line section P - Q in FIG. 5A, and an output is produced to the comparator 53 as shown in FIG. 4. Since a target position signal of the rotation supporting unit 2 is updated in a predetermined cycle, the rotation supporting unit 2 continues a rotation in the C direction at a constant speed based on the movement of the servo amplifier 54 and the driving circuit 55. In this case, the X-ray tube unit 3 also rotates in the C direction at a constant speed.

When the logical arithmetic unit 56 detects that the image system unit 4 has reached the P point, by monitoring an actual position signal of the rotation supporting unit 2 from the rotary encoder 36 shown in FIG. 4, the logical arithmetic unit 56 drives the X-ray controller 22 through the X-ray control interface 57. Then, a pulse-state high voltage of 4 msec, for example, is generated from the X-ray controller 22 and this pulse-state high voltage is applied to the X-ray tube unit 3, so that an X-ray pulse is radiated from the X-ray tube unit 3, as shown in FIG. 5D.

The X-ray pulse thus radiated is transmitted through the subject 11 loaded on the table 13, and the transmitted X-rays are incident to the I.I. 23. Then, the incident transmitted X-ray image is converted to an optical image and this optical image is picked up by the television camera 24.

An image signal outputted from the television camera 24 is inputted to the first image processing unit 6. The image signal is then converted into a digital signal by the A/D converter 25 to form image data of a frame unit of a 512×512 matrix, for example. This image data is sequentially stored in the memory unit 26 as shown in FIG. 5E. In this case, the rotary encoder 36 detects the rotation angle of the rotation supporting unit 2. At every one degree of the rotation angle, for example, the system control unit 10 controls to continuously carry out X-rays radiation and reading of image data. The memory unit 26 also stores the detected angle information as image data of $A_1$, $A_2$, . . . , $A_n$, for example, through the arithmetic processing unit 29, as shown in FIG. 5E.

Each of the image data $A_1$ to $A_n$ stored as described above is sequentially read out from the memory unit 26, inputted to the D/A converter 27 and is then converted into an analog image signal. Then, the image signal is inputted to the display unit 8 and is continuously displayed. The images of the $A_1$ to $A_n$ continuously displayed have different directions of X-rays radiation from the X-ray tube unit 3 which rotates for each frame picture, and therefore, the images appear as stereoscopic images to the operator as a result of an afterimage effect.

Images are picked up continuously as shown in FIGS. 5D and 5E in the manner as described above. When the logical arithmetic unit 56 within the system control unit 10 monitors an actual position signal from the rotary encoder 36 to confirm that the rotation supporting unit has reached the Q point shown in FIG. 4, the logical arithmetic unit 56 sequentially updates, in a predetermined deceleration pattern as shown in FIG. 5B, the position signal to be targeted next until the position information corresponding to the backward rotation position Q' point is reached, and sends data to the comparator 53 within the body control unit 9. Then, the servo amplifier 54 and the driving circuit 55 start deceleration of the rotation supporting unit 2 and temporarily stops at the Q' point, as shown in FIG. 5B.

Then, the logical arithmetic unit 56 sequentially updates, in a predetermined acceleration pattern, position information to be targeted from the Q' point to the P' point in the D direction (a backward direction) on the rotation supporting unit 2, and produces an output to the comparator 53. Thus, the rotation supporting unit 2 reverses the rotation at the Q' point and starts rotation in the D direction in a manner similar to the rotation in the C direction, and the speed curve rises from the Q' point in FIG. 5B. Immediately before reaching the Q point in FIG. 4, the rotation speed is accelerated to the same level as the rotation in the C direction. In this case, the rotation speed is settled immediately before reaching the Q point, as shown in FIG. 5B. During the period of a forward rotation from the Q point to the Q' point and a period of deceleration, stopping, reversed rotation and. acceleration at the time of a backward rotation from the Q' point to the Q point, photographing is continued in the same cycle as the photographing from the P point to the Q point and reading of image data is continued, as shown in FIGS. 5D and 5E.

In this case, at a suitable timing during a period from the Q point in the forward rotation to the Q point in a backward rotation, the contrast medium injector 51 shown in FIG. 4 is operated to start an injection of the contrast medium into the body (an artery) of the subject 11, as shown in FIG. 5C. The injection of the contrast medium finishes at a suitable timing before the P point during a backward rotation.

When the logical arithmetic unit 56 detects that the image system unit 4 reversed the rotation to have reached the Q point, by monitoring an actual position signal of the rotation supporting unit 2 from the rotary encoder 36, as described above, the logical arithmetic unit 56 synchronizes the radiation of the X-ray pulse and the reading of images at the Q point, sequentially updates position information to be targeted next in a predetermined cycle in a manner similar to the case of the A direction, and produces an output to the comparator 53. Then, based on the operation of the servo amplifier 54 and the driving circuit 55, the rotation supporting unit 2 continues a rotation in the D direction at a predetermined speed, to carry out a photographing in a cycle similar to the case of the rotation in the C direction, reads image data such as $B_n, \ldots, B_2, B_1$, for example, and stores these data, as shown in FIG. 5E. As a result, images after injecting the contrast medium can be collected. Radiation of X-rays and reading of images are controlled so that pairs of image data $(A_1, B_1), (A_2, B_2), \ldots, (A_n, B_n)$ can be read in the same phase angle (a rotation angle of the rotation supporting unit) respectively.

The image system unit 4 rotates in the D direction to continuously pick up images, as described above. When the logical arithmetic unit 56 recognizes that the image pick up unit 4 has reached the P point shown in FIG. 4, the rotation supporting unit 2 starts deceleration in the manner similar to the case of reaching the Q point in the rotation in the C direction, temporarily stops at the P' point, then reverses the rotation in the C direction again, and further accelerates. During the period of a backward rotation from the P point to the P' point and a period of deceleration, stopping, reversed rotation and acceleration at the time of a forward rotation from the P' point to the P point, photographing is continued at the same speed as described above and reading of image data is continued, as shown in FIGS. 5D and 5E.

When the rotation supporting unit 2 made a reversed rotation and the image system unit 4 rotated to have reached the P point again, the logical arithmetic unit 56 recognizes this, and the image system unit 4 makes a first radiation of X-ray pulse and reads an image at the P point and continues photographing in a manner similar to the case of the rotation in the C direction. The above-described series of operation are carried out by repeating a forward rotation of the rotation supporting unit 2 in the C direction and a backward rotation in the D direction by desired number of times until the contrast medium injected into the artery of the subject 11 reaches the vein and flows out of the body, and fluoroscopy is carried out continuously during this period.

Next, in order to carry out a subtraction processing by subtraction between two images that have been taken as described above, the images $A_1$ to $A_n$ from the P point to the Q point that have been taken at first in the state that the contrast medium was not injected into the body (ref. FIG. 5E) are used as mask images and the images $B_n$ to $B_1$ from the Q point to the P point that have been taken during a backward rotation after the contrast medium was injected into the body (ref. FIG. 5E) are used as live images, and a subtraction is carried out between the images of the corresponding same rotational phase angle of the rotation supporting unit 2, by the data processing unit 29 within the first image processing unit 6 shown in FIG. 1. As a result, subtraction images $B_1 - A_1, B_2 - A_2, \ldots, B_n - A_n$ can be obtained sequentially, as shown in FIG. 5F. Alternately, subtraction may be carried out between mask images or between live images.

In the above explanation, the photographing mode has been set to the continuous going and returning photographing mode. However, when it is not necessary to photograph a vein phase, it is possible to reduce the number of backward rotation of the image system unit 4 to one and the photographing can be finished in a short time, if the photographing mode selecting switch 58 of the operating unit 37 is operated to the one going and returning photographing mode, for example. Further, the above series of operation have been explained based on the assumption of subtraction between a mask image and a live image. However, if subtraction is not carried out, the contrast medium may be injected into the body of the subject at a suitable timing during photographing from the starting P point to the Q point.

The present invention can be applied to the X-ray photography device in which the X-ray tube unit 3 and the image system unit 4 are rotated in a single direction by means of a slipping power supplying method as generally used in the X-ray tomography device.

Further, in the embodiment of FIG. 4, the rotary encoder 36 has been used as a detecting unit for detecting a rotation angle of the rotation supporting unit 2. However, the detecting unit is not limited to the rotary encoder in the present invention, but a microswitch or the like may also be used instead, to detect positions of the P' point, P point, Q point and Q' point of the rotation supporting unit 2. In this case, the detection of a rotation angle of the rotation supporting unit 2 can be achieved by fine controlling the rotation speed of the rotation supporting unit 2 by matching the timing of the X-rays radiation from the X-ray tube unit 3 and the reading of images to the synchronizing signal of the television camera 24. Further, in the above explanation, although the photographing angle range based on the rotation of the X-ray tube unit 3 and the image system unit 4 has been set to the range of 0 degree to 180 degrees, the angle range is not limited to this but the angle range may also be set to the range of 90 degrees or 360 degrees, for example. In this case, the logical arithmetic unit 56 of the system control unit 10 changes a target position signal to be given to the comparator 53 of the body control unit 9.

When the inspection by the above-described rotational stereoscopic photographing has been finished and the inspection of the same subject 11 by tomography is to be carried out next, the subject table 13 is suitably moved forward and backward, up and down and rightward and leftward to fix the inspection position, with the subject 11 kept loaded on the subject table 13. Next, the operator operates the selecting switch of a tomography mode not shown on the operating unit 37, so that the X-ray tube unit 3 moves by the guidance of the guide rails 15 and 15 based on the rotation of the driving motor 18 shown in FIG. 2 and is automatically set to a position facing from the front the multi-channel X-ray detector 5 as shown by a broken line in FIG. 1. At the same time, the collimator 21 is set to collimate the X-ray beam to meet the tomography.

Figure 6:
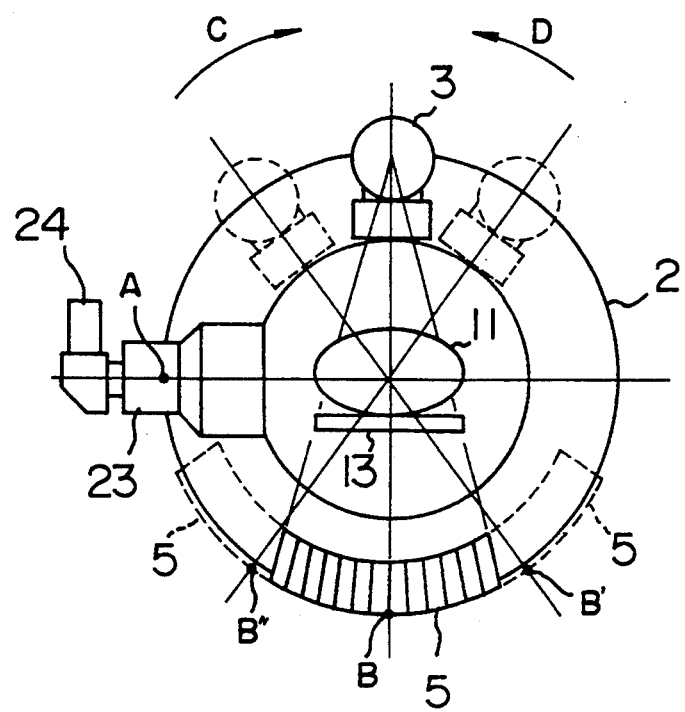
FIG. 6 is a diagram for explaining the operation of picking up image by the digital X-ray photography device according to the present invention.

In this state, the operator operates the photographing preparation switch not shown on the operating unit 37 so that the system controller 10 suitably rotates the rotation supporting unit 2 through the body controller 9, and the X-ray detector 5 moves to the B' point position and stops there, as shown in FIG. 6. In this case, the X-ray tube unit 3 is positioned at a point facing the B' point from the front. This is the state of the waiting position before starting photographing.

Next, the operator starts photographing by the operating unit 37 and the rotation supporting unit 2 starts rotation in the C direction, for example, in FIG. 6. Then, the X-ray detector 5 is started from the B' point and is accelerated and is then stabilized at a predetermined rotation speed immediately before reaching the B point. In this case, the encoder 36 shown in FIG. 1 detects that the X-ray detector 5 has reached the B point and transmits this detection signal to the body controller 9. Then, the body controller 9 sends this detection signal to the system controller 10, and the system controller 10 sends a control signal for starting photographing to the X-ray controller 22. From this point, the X-ray controller 22 generates a pulse-shaped high voltage and supplies this high voltage to the X-ray tube unit 3. With this arrangement, the X-ray tube unit 3 radiates pulse-shaped X-rays, which are irradiated on to the subject 11 on the subject table 13.

An X-ray image which has transmitted through the subject 11 is incident to the X-ray detector 5 and is converted into an electric signal. This electric signal is inputted to the second image processing unit 7 and is digitalized there, and a tomogram is reconstructed at the same time. Tomograms of the subject 11 sequentially obtained during the rotation in the arrow C direction shown in FIG. 4 are displayed two dimensionally in the display unit 8.

X-rays photographing is carried out by the X-ray tube unit 3 and the X-ray detector 5 as described above. When the X-ray detector 5 has rotated by 360 degrees in the arrow C direction and reached the B point in FIG. 6 again, the encoder 36 detects this state and stops the X-rays radiation from the X-ray tube unit 3 through the body controller 9, the system controller 10 and the X-ray controller 22. Then, the system controller 10 controls to stop the rotation of the rotation supporting unit 2 through the body controller 9 so that the rotation supporting unit 2 starts deceleration from the B point and stops rotation at the B" point in FIG. 6. Thereafter, if photographing of the same portion is necessary again or photographing of another portion is necessary, the above-described procedure is repeated.

In the above explanation, it has been assumed that the rotation supporting unit 2 is rotated by 360 degrees in the arrow C direction to radiate X-rays. However, the rotation angle is not limited to the above, and the rotation supporting unit 2 may also be rotated in the opposite arrow D direction or in the range of rotation angle of 270 degrees or 180 degrees, for example, to radiate X-rays. Alternately, two X-ray tube units 3 may be provided and fixed to face the image system unit 4 and the X-ray detector 5 respectively on the rotation supporting unit 2. Alternately, it is also good to fix the X-ray tube unit 3 at one position on the rotation supporting unit 2 and move the image system unit 4 and the X-ray detector 5 to face the X-ray tube unit 3 within a suitable angle range, in FIG. 1.

We claim:

1. A digital X-ray photography device, comprising:
    a body gantry installed on a floor surface and having an opening for inserting a subject table therein in a horizontal direction at almost a center portion of a standing portion;
    a ring-shaped rotation supporting unit rotatably provided around said opening within said body gantry;
    an X-ray tube unit, provided movably around a rotation center of said rotation supporting unit in a predetermined range of angle on said rotation supporting unit, for radiating X-rays to said subject;
    an image system unit, fixed at a predetermined position on said rotation supporting unit, for converting an optical X-ray image transmitted through said subject into an image signal;
    an X-ray detector, fixed at a predetermined position on said rotation supporting unit, for detecting X-rays transmitted through said subject and converting said detected X-rays into an electric signal;
    a first image processing unit for processing said image signal from said image system unit and constructing a display image;
    a second image processing unit for processing said electric signal from said X-ray detector and reconstructing a tomogram;
    one or a plurality of display units for inputting an image signal from said first and second image processing units respectively and displaying outputs as images;
    body control means for controlling said X-ray tube unit to move and come to a position where said X-ray tube unit can face said image system unit or said X-ray detector and for controlling a rotation operation of said rotation supporting unit;
    X-ray control means for controlling a generation of X-rays; and system control means for controlling operation of each of said structural elements.

2. A digital X-ray photography device according to claim 1, wherein said system control means includes means for controlling said X-ray control means so that pulse-shaped X-rays can be radiated continuously during a period while said rotation supporting unit is rotating in a predetermined range of angle.

3. A digital X-ray photography device according to claim 2, wherein said body control means includes means for continuously carrying out a forward rotation and a backward rotation of said rotation supporting unit at least once in said predetermined range of angle.

4. A digital X-ray photography device according to claim 3, wherein said system control means includes means for controlling X-rays to be continuously radiated during a period while said rotation supporting unit is making a forward rotation, is changing a direction of rotation from a forward rotation to a backward rotation and is making a backward rotation.

5. A digital X-ray photography device according to claim 1, wherein said first image processing unit includes means for subtracting image data that have been read in the same rotational phase angle of said rotation supporting unit and constructing said display image.

6. A rotational stereoscopic photographing method, in a digital X-ray photography device, comprising a body gantry installed on a floor surface and having an opening for inserting a subject table therein in a horizontal direction at almost a center portion of a standing portion, a ring-shaped rotation supporting unit rotatably provided around said opening within said body gantry, and an X-ray tube unit for radiating X-rays and an image system unit for converting an optical transmission X-ray image into an image signal at positions facing each other by sandwiching said opening on said rotation supporting unit, including the steps of:

setting said rotation supporting unit at a first position;
accelerating said rotation supporting unit from said first position to a second position;
rotating said rotation supporting unit at a predetermined speed from said second position to a third position;
radiating pulse-shaped X-rays and reading image data in a constant cycle from a time when said rotation supporting unit passes through said second position;
reducing rotation of said rotation supporting unit when said rotation supporting unit has come to said third position and stopping rotation at a fourth position;
accelerating and rotating said rotation supporting unit in a backward direction from said fourth position to said third position;
rotating said rotation supporting unit at said predetermined speed from said third position to said second position;
synchronizing radiation of X-rays and reading of images at said third position and thereafter continuing radiation of pulse-shaped X-rays and reading of image data in said predetermined cycle; and
reducing and then stopping speed of rotation of said rotation supporting unit when said rotation supporting unit has come to said second position.

7. A rotational stereoscopic photographing method according to claim 6, further including a step of repeating a series of forward rotation and backward rotation at each of said steps by a predetermined number.

8. A rotational stereoscopic photographing method according to claim 6, further including a step of subtracting image data read in the same rotational phase angle of said rotation supporting unit and constructing a display image.

* * * * *